United States Patent [19]

Wiegand

[11] 4,008,271
[45] Feb. 15, 1976

[54] PROCESS FOR PREPARING A MIXED ANHYDRIDE OF A SULFONIC ACID AND A CARBOXYLIC ACID

[75] Inventor: Karl E. Wiegand, Baton Rouge, La.

[73] Assignee: Ethyl Corporation, Richmond, Va.

[22] Filed: June 23, 1975

[21] Appl. No.: 589,090

Related U.S. Application Data

[62] Division of Ser. No. 451,817, March 18, 1974, Pat. No. 3,935,216.

[52] U.S. Cl. .......................................... 260/545 R
[51] Int. Cl.$^2$ ............... C07C 51/54; C07C 153/00; C07C 154/00
[58] Field of Search ............................... 260/545 R

[56] References Cited

UNITED STATES PATENTS

| 2,941,000 | 6/1960 | May et al. | 260/545 R |
| 3,124,564 | 3/1964 | McKay | 260/545 R |
| 3,160,660 | 12/1964 | Park et al. | 260/545 R |
| 3,541,120 | 11/1970 | Firth | 260/545 R |
| 3,743,686 | 7/1973 | Koch et al. | 260/545 R |
| 3,821,279 | 6/1974 | Kurono et al. | 260/545 R |

OTHER PUBLICATIONS

Karger et al., "J. Org. Chem.", vol. 36, No. 4, pp. 528–531 (1971).

Primary Examiner—Norman Morgenstern
Attorney, Agent, or Firm—Donald L. Johnson; John F. Sieberth; James M. Pelton

[57] ABSTRACT

A process for preparing a mixed anhydride acylating agent and a process for acylating pyrrole derivatives, such as, 1-methylpyrrole-2-acetonitrile using the mixed anhydride acyiating agent.

8 Claims, No Drawings

PROCESS FOR PREPARING A MIXED ANHYDRIDE OF A SULFONIC ACID AND A CARBOXYLIC ACID

This is a division, of application Ser. No. 451,817, filed on Mar. 18, 1974, now U.S. Pat. No. 3,935,216.

BACKGROUND OF THE INVENTION

Numerous derivatives of aroyl-substituted pyrroles have been prepared by Friedel-Crafts' reaction between an appropriate aroyl halide and a pyrrole-2-acetic acid derivative in the presence of a Lewis acid, preferably using a metallic halide catalyst such as aluminum chloride, see U.S. Pat. No. 3,752,826. Such compounds are useful as anti-inflammatory agents and as synthetic intermediates. However, the use of a metallic halide catalyst requires considerable efforts to purify the product and remove the metallic constituent from the reaction product, especially for therapeutic use of the product as an anti-inflammatory agent. According to the present invention, a process which does not employ metallic halides as a catalyst has now been discovered.

The present invention relates to the acylation of a pyrrole derivative, for example, a pyrrole-2-acetic acid derivative using a mixed anhydride. Classically, acid anhydrides have been prepared by reaction of an acid halide and a salt or by driving the equilibrium existing between a carboxylic acid and an acid anhydride to prepare the desired acid anhydride. Mixed anhydrides have been prepared by Karger and Mazur, *J. Org. Chem.*, Vol. 36, No. 4, p. 528–540 (1971), which describes the synthesis of mixed sulfonic-carboxylic anhydrides, utilizing sulfonic acid and either acyl chloride or anhydride.

According to Karger and Mazur, supra, p. 529, it is possible to prepare mixed anhydrides by heating an excess of carboxylic anhydride with the sulfonic acid for 20–30 minutes at 120° C followed by removal under high vacuum of the excess anhydride together with the free acid formed according to the following equation:

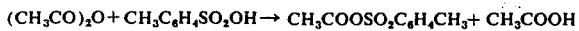

$$(CH_3CO)_2O + CH_3C_6H_4SO_2OH \rightarrow CH_3COOSO_2C_6H_4CH_3 + CH_3COOH$$

Accordingly, acetyl para-toluenesulfonate and trichloroacetyl para-toluenesulfonate were prepared. However, mixed anhydride preparation from higher molecular weight anhydrides and acids is complicated by involatility of both anhydride and acid. This, according to the authors necessitates higher temperatures causing decomposition of product. As a further aspect of the present invention, there is provided a process for preparation of mixed anhydrides from higher molecular weight anhydrides without the necessity for higher temperature or distilling off the acid formed on reaction.

SUMMARY OF THE INVENTION

Accordingly, I have now discovered a process for preparing a mixed anhydride of an aromatic acid and an organo-substituted inorganic acid, said process comprising reacting the anhydride of said aromatic acid with said organo-substituted inorganic acid in the presence of a solvent in which said aromatic acid is substantially insoluble. In another aspect of this invention, there is provided a process for acylating pyrrole derivatives, such as 1-methylpyrrole-2-acetonitrile, which comprises reacting a mixed anhydride of an aromatic acid and an organo-substituted inorganic acid in the presence of a solvent, whereby the substituted pyrrole is acylated with the aroyl radical, for example, the para-toluoyl radical.

DESCRIPTION OF PREFERRED EMBODIMENTS

The process for acylating pyrrole derivatives according to this invention comprises reacting a mixed anhydride of an aromatic acid and an organo-substituted inorganic acid with a pyrrole derivative in the presence of a solvent. Accordingly, the mixed anhydride must first be prepared. For preparation of the mixed anhydride, there is required an aromatic acid and an organo-substituted inorganic acid. Typical of the aromatic acids which may be employed in the preparation of the mixed anhydride are benzoic acid, monosubstituted benzoic acid and polysubstituted benzoic acid, in which each substituent of said substituted benzoic acid is a member selected from the group consisting of halo, lower alkyl, trifluoromethyl, lower alkoxy, nitro, amino, cyano and methylthio groups. Particularly preferred are benzoic acid and para-toluic acid, and most preferred is toluic acid. As used in this invention "lower alkyl" and "lower alkoxy" may be straight or branched chain saturated hydrocarbons having from 1-6 carbon atoms such as, for example, methyl, ethyl, propyl, isopropyl, butyl, pentyl, hexyl and the like alkyls and, respectively, the corresponding alkoxy groups such as methoxy, ethoxy, propoxy, isopropoxy and the like. Therefore, a particularly preferred aromatic acid for producing the mixed anhydride is para-toluic acid.

The organo-substituted inorganic acid from which the other portion of the mixed anhydride is prepared is selected from trifluoroacetic acid, trichloroacetic acid, methane sulfonic acid, toluene sulfonic acid, trichloromethane sulfonic acid and trifluoromethane sulfonic acid. In many cases, such organo-substituted inorganic acids are expensive, such as trifluoroacetic acid and trichloroacetic acid. Therefore, a preferred inorganic acid is methane sulfonic acid or toluene sulfonic acid, and a most preferred organo-substituted inorganic acid is methane sulfonic acid. The preparation of the mixed anhydride is preferably carried out in a solvent in which the reactants are soluble and the product is also soluble but in which the product can be separated from unreacted reactants. Preferably, the solvent is selected from halogenated hydrocarbons and nitroalkanes. Most preferably, the solvent is a nitroalkane. Typical of the halogenated hydrocarbons are methylene chloride, methyl chloride, 1,2-dichloroethane, carbon tetrachloride and the like. Typical of the nitroalkanes are nitromethane, nitroethane, nitropropane and similar nitro-substituted alkanes in which the alkane may be a straight or branched chain saturated hydrocarbon having from 1-6 carbon atoms, such as, for example, methyl, ethyl, propyl, isopropyl, butyl, pentyl, hexyl and similar saturated hydrocarbons. Most preferred among the various solvents which may be employed in the preparation of the mixed anhydride is nitromethane.

Mixed anhydrides useful in the process for acylating pyrrole derivatives according to this invention can be prepared according to classical techniques described in the literature and as indicated in the Background of the Invention employing the aromatic acid and organo-substituted inorganic acid described hereinabove. More preferably, the mixed anhydride may be prepared by first preparing an acid anhydride of the aromatic acid by simply dehydrating the aromatic acid at elevated temperatures in the presence of a dehydration agent, such as, for example, thionyl chloride. Then, according to this invention, the aromatic acid anhydride reacts with the organo-substituted inorganic acid in the presence of a solvent forming the mixed anhydride and producing one equivalent of free aromatic acid. By employing a solvent in which the starting aromatic acid is substantially insoluble the free aromatic acid is precipitated out of the reaction mixture. Thus, the problem of separating the mixed anhydride from the starting reactants and reaction products at higher temperatures causing decomposition of the product mixed anhydride is obviated.

As a typical illustration, the mixed anhydride of paratoluic acid and methane sulfonic acid can conveniently be prepared by reacting para-toluic anhydride with methane sulfonic acid in nitromethane at room temperature for about 20 minutes. One equivalent of para-toluic acid precipitates from the reaction mixture and can be filtered therefrom while the para-toluic methane sulfonic acid anhydride remains in the nitromethane solvent and can easily be separated from it under conditions which do not decompose the mixed anhydride. Such a process is illustrated by the following example.

EXAMPLE 1

Preparation of Para-Toluic Methane Sulfonic Anhydride 25.4 g (0.1 mole) of para-toluic anhydride was dissolved in 100 ml of warm nitromethane and then 9.6 g (0.1 mole) of methane sulfonic acid was added. The reaction mixture was stirred for 20 minutes and then filtered, giving 13.72 g (0.1 mole) of para-toluic acid precipitant. The reaction was quantitative, resulting in the para-toluic methane sulfonic anhydride dissolved in nitromethane.

Following the procedure of Example 1, similar results can be obtained when the solvent employed is a halogenated hydrocarbon, such as, dichloroethane, carbon tetrachloride, methylene chloride or the like, or another nitroalkane, such as, nitroethane, nitropropane, nitroisopropane, nitrobutane, or the like. Also, similar results are obtained when methane sulfonic acid is replaced with toluene sulfonic acid.

The mixed anhydride prepared above may be used in a variety of preparations, for example, in the acylation of xylenes and other nonactivated arenes such as benzene, in the cleavage of ethers and in reaction with amines. One specific example is the acylation of pyrrole derivatives to produce aroyl-substituted pyrroles. More particularly, the mixed anhydride prepared above may be used in the preparation of 5-aroyl-1-methylpyrrole-2-acetonitrile by reaction of 1-methyl-pyrrole-2-acetonitrile with a mixed anhydride of an aromatic acid and organo-substituted organic acid, preferably para-toluic methane sulfonic anhydride.

For such reactions, the 1-methylpyrrole-2-acetonitrile can be prepared by the method of Orth et al, U.S. Pat. No. 3,523,952, or according to Herz et al, *Journal of the Am. Chem. Soc.*, Vol. 73, p. 4921–4923 (1951), or Herz, *Journal of the Am. Chem. Soc.*, Vol. 75, p. 483 (1953).

The aroyl substituent is that which is substituted on the pyrrole nucleus of the mixed anhydride and can be any suitable aroyl group described hereinabove relating to preparation of the mixed anhydride, for example, the aromatic portion of the aroyl substituent can be phenyl, thienyl, 5-methylthienyl, mono-substituted phenyl and poly-substituted phenyl in which each substitutent of the substituted phenyl group is a member selected from the group consisting of halo, lower alkyl, trifluoromethyl, lower alkoxy, nitroamino, cyano and methylthio groups. As used herein "lower alkyl" and "lower alkoxy" have the same meaning as given hereinabove.

The solvent in which the reaction of the mixed anhydride and pyrrole derivative are reacted can be a halogenated hydrocarbon or nitroalkane as indicated above for preparation of the mixed anhydride. Preferred solvents for the reaction of the mixed anhydride and pyrrole derivative are nitromethane, 1,2-dichloroethane and methylene chloride or mixtures of these. A most preferred solvent is nitromethane.

The reaction can be carried out at temperatures which are suitable for efficient reaction rate and which are not detrimental to the reactants or products. Preferably, the reaction is carried out at a temperature from about 20°–100° C and more preferably from about 60° to about 85° C. The reactants are employed in about stoichiometric quantities and the reaction proceeds for a period from about 0.25 to about 3 hours and preferably about 2 hours.

In accordance with the above, the following examples were run illustrating the general nature of the reaction.

EXAMPLE 2

To the crude mixture of nitromethane solvent and paratoluic methane sulfonic anhydride, prepared in Example 1, was mixed 12.1 g (0.1 mole) of N-methylpyrrole-2-acetonitrile. The mixture was heated for two hours at 80° C. The reactor contents were then cooled to 0° C and 3.2 g of para-toluic acid (0.023 mole) were filtered off. The solution was washed with sodium bicarbonate solution, water and dried over sodium sulfate. The solvent was distilled off giving 18.5 g of crude 5 para-toluoln-methylpyrrole-2-acetonitrile with the yield of crude product being 77 percent.

EXAMPLE 3

The procedure of Example 1 was repeated except that the precipitated p-toluic acid was not removed from the solution. Then to the resulting slurry was added an equimolar amount of N-methylpyrrole-2-acetonitrile followed by heating at 80° C. The conversion was followed by NMR spectroscopic examination of protons in the pyrrole region. The reaction appeared complete after ½ hour and the reaction mixture was cooled, washed with aqueous sodium bicarbonate and analyzed by both VPC and high pressure liquid chromatography indicating a yield of 41–42 percent of 5-p-toluoyl-N-methylpyrrole-2-acetonitrile.

Similar results can be obtained when the mixed anhydride employed is para-toluic para-toluene sulfonic anhydride, para-chlorobenzoic methane sulfonic anhydride, meta-chlorobenzoic methane sulfonic anhydride, para-bromobenzoic methane sulfonic anhydride, para-nitrobenzoic para-toluene sulfonic anhydride, benzoic methane sulfonic anhydride, thiophene-2-carboxylic methane sulfonic anhydride, ortho-toluic methane sulfonic anhydride, para-chlorobenzoic para-toluene sulfonic anhydride and the like. Also similar results are obtained when the solvent employed in the above reactions is methylene chloride, 1,2-dichloroethane, carbon tetrachloride and similar solvents, including nitrobenzene, nitrotoluene, nitroethane, nitropropane and similar nitro-substituted aromatic and aliphatic solvents.

Accordingly, it is a preferred embodiment of this invention to acylate 1-methylpyrrole-2-acetonitrile by reacting a mixed anhydride of para-toluic methane sulfonic anhydride in nitromethane at a temperature from about 60° to about 85° C.

One skilled in the art can readily envision variations in the above processes of this invention which are within the scope hereof. Thus, the invention should be limited only by the lawful scope of the following claims.

What is claimed is:

1. A process for preparing a mixed anhydride of a sulfonic acid and a carboxylic acid which comprises reacting a sulfonic acid selected from the group consisting of methane sulfonic acid and toluene sulfonic acid with the anhydride of a carboxylic acid selected from the group consisting of benzoic acid, mono-substituted benzoic acid and poly-substituted benzoic acid wherein the substituent groups are selected from the group consisting of halo, lower alkyl, trifluoromethyl, lower alkoxy, nitro, amino, cyano and methylthio in the presence of a solvent selected from the group consisting of halogenated hydrocarbons and nitroalkanes, separating the free by-product carboxylic acid formed and recovering the mixed anhydride from the solvent phase.

2. The process of claim 1 wherein said aromatic acid is para-toluic acid.

3. The process of claim 1 wherein said organo-substituted inorganic acid is methane sulfonic acid.

4. The process of claim 1 wherein said aromatic acid is para-toluic acid and said organo-substituted inorganic acid is methane sulfonic acid.

5. The process of claim 1 wherein said solvent is selected from the group consisting of halogenated hydrocarbons and nitroalkanes.

6. The process of claim 1 wherein said solvent is a nitroalkane.

7. The process of claim 1 wherein said solvent is nitromethane.

8. The process of claim 1 wherein said solvent is nitromethane, said aromatic acid is para-toluic acid and said organo-substituted acid is methane sulfonic acid.

* * * * *